United States Patent [19]

Saikawa et al.

[11] 4,428,936

[45] Jan. 31, 1984

[54] ANTIBACTERIAL COMPOSITION FOR MEDICAL USE

[75] Inventors: Isamu Saikawa; Takashi Yasuda; Masaru Tai; Yutaka Takashita, all of Toyama; Hiroshi Sakai, Takaoka; Michiko Mae, Toyama; Masahiro Takahata, Kosugimachi; Susumu Mitsuhashi, Musashino, all of Japan

[73] Assignee: Toyama Chemical Co., Ltd., Tokyo, Japan

[21] Appl. No.: 187,755

[22] Filed: Sep. 16, 1980

Related U.S. Application Data

[63] Continuation of Ser. No. 22,102, Feb. 20, 1979, abandoned.

[30] Foreign Application Priority Data

Mar. 24, 1978 [JP]  Japan .................................. 53-33043

[51] Int. Cl.³ ............................................. A61K 35/00
[52] U.S. Cl. .................................................... 424/114
[58] Field of Search ......................................... 424/114

[56] References Cited

PUBLICATIONS

Chemical Abstracts 87: 184533(b) (1977).
Merck Index, 8 Ed., Merck and Co. Inc., Rahway, N.J., 1968, pp. 674, 271 and 771.

*Primary Examiner*—Jerome D. Goldberg
*Attorney, Agent, or Firm*—Oblon, Fisher, Spivak, McClelland & Maier

[57] ABSTRACT

An antibacterial composition for medical use comprising a cephalosporin or a pharmaceutically acceptable salt thereof and a β-lactamase-inhibiting compound having a β-lactam ring. The composition exhibits synergistic effect which is much greater than the sum of antibacterial effects of each component used alone.

1 Claim, 5 Drawing Figures

ANTIBACTERIAL COMPOSITION FOR MEDICAL USE

This is a continuation of application Ser. No. 22,102 filed on Mar. 20, 1979 now abandoned.

This invention relates to novel antibacterial compositions for medical use. More particularly, it relates to antibacterial compositions for medical use comprising cephalosporins represented by the formula [I]:

[I]

wherein $R^1$ represents an acetoxy, 5-(1-methyl-1,2,3,4-tetrazolyl)thio or 2-(5-methyl-1,3,4-thiadiazolyl)-thio group and $R^2$ represents a hydrogen atom or a hydroxyl group, or pharmaceutically acceptable salts thereof and β-lactamase-inhibiting compounds having a β-lactam ring.

The cephalosporins represented by the formula [I] and pharmaceutically acceptable salts thereof, which were developed by the present inventors, are useful substances having excellent characteristics such as a broad antibacterial spectrum.

The present inventors have found as a result of extensive studies that when a cephalosporin represented by the formula [I] or a pharmaceutically acceptable salt thereof is mixed with a β-lactamase-inhibiting compound having a β-lactam ring, the latter makes it difficult for the cephalosporins represented by the formula [I] and pharmaceutically acceptable salts thereof to be affected by β-lactamase, and the resulting composition exhibits a synergistic effect on the antibacterial activity.

An object of this invention is to provide an antibacterial composition having a pronounced antibacterial activity against Gram-negative bacteria existing even in a large population, especially against *Escherichia coli*, *Proteus* species, *Klebsiella pneumoniae* and *Pseudomonas aeruginosa*.

Another object of this invention is to provide an antibacterial composition active to those pathogenic bacteria which are resistant to conventional penicillins or cephalosporins.

A further object of this invention is to provide an antibacterial composition capable of enhancing the bactericidal speed and therapeutic effectiveness.

Other objects and advantages of this invention will become apparent from the following description.

According to this invention, there is provided an antibacterial composition for medical use comprising a cephalosporin represented by the formula [I] or a pharmaceutically acceptable salt thereof and a β-lactamase-inhibiting compound having a β-lactam ring.

The above-mentioned pharmaceutically acceptable salts are those which are commonly used as cephalosporin salts, including salts with metals such as sodium, potassium and calcium, ammonium salt and salts with amines such as procaine, N,N-dibenzylethylenediamine and the like.

The β-lactamase-inhibiting compounds having a β-lactam ring used in this invention include β-lactamse-inhibiting penicillins and cephalosporins and clavulanic acids. The β-lactamase-inhibiting penicillins and cephalosporins are, for example, Cloxacillin, Dicloxacillin, Oxacillin, Flucloxacillin, Methicillin, Cefoxitin and 7β-(α-cyanomethylthioacetamido)-7α-methoxy-3-[5-(1-methyl-1,2,3,4-tetrazolyl)thiomethyl]-Δ³-cephem-4-carboxylic acid and pharmaceutically acceptable salts thereof. These pharmaceutically acceptable salts have the same meanings as mentioned above as to salts of the cephalosporins represented by the formula [I].

And the clavulanic acids include, for example, the compound which is represented by the following formula and pharmaceutically acceptable salts thereof:

These pharmaceutically acceptable salts have the same meanings as mentioned above as to salts of the cephalosporins represented by the formula [I].

The suitable ratio of the cephalosporin represented by the formula [I] to the β-lactamase-inhibiting compound having a β-lactam ring in the composition of this invention varies to some degrees depending on the type of target pathogenic bacteria or symptoms, but is generally in the range of form 1:0.04 to 1:5 (in terms of weight ratio or potency ratio), preferably 1:0.1 to 1:1.5 (in terms of weight ratio or potency ratio).

In this invention, the type of β-lactamse-inhibiting compounds having a β-lactam ring may be properly selected according to particular pathogenic bacteria.

The antibacterial composition for medical use according to this invention is used preferably as a parenteral injection, although it can be used in other dosage forms and through other administration routes similarly to known antibiotics such as conventional penicillins and cephalosporins. It can also be used in the form of ointment and preparation for rectal administration.

When used as an injection, the antibacterial composition of this invention can be mixed with solid or liquid carriers or diluents which are conventionally used in injections of known antibiotics. Of the carriers, sterilized water is most frequently used. The antibacterial composition of this invention may, of course, be in the form of powder which can be dissolved in suitable vehicles such as sterilized water, glucose solution and physiological saline solution for use as an injection.

In administering the antibacterial composition of this invention as an injection to man, intravenous injection (including drip infusion) or intramuscular injection is generally suitable.

The dosage of the antibacterial composition of this invention is properly selected in accordance with the ratio between the cephalosporin represented by the formula [I] and the β-lactamase-inhibiting compound having a β-lactam ring, age of the patient, and the type or symptoms of the infectious disease. The suitable dose of an injection ranges generally from 0.5 to 10 g potency per day for adults, but the dose is not limited thereto.

In administering the antibacterial composition of this invention as an intramuscular injection, it can be used together with those drugs which are usually used in injections such as analgesics, for example, lidocaine hydrochloride.

The efficacy of the antibacterial composition of this invention is illustrated below with reference to Test Examples and the accompanying drawings which are diagrammatic representation of the test results. In the drawings.

Test Example 1

GROWTH-INHIBITION TEST ON CLINICALLY ISOLATED STRAIN

Heart Infusion agar containing a prescribed amount of Methicillin sodium or T-1551 Na was inoculated with the test bacterium at a rate of about $10^8$ cells/ml. After incubation for 18 hours at 37° C., the growth of the test bacterium was inspected. The results of test were as shown in Tables 1, 2 and 3. In each table, (+) means that the test bacterium grew and (−) means that the test bacterium did not grow. From Tables 1, 2 and 3, it is apparent that the combination of Methicillin sodium and T-1551 Na exhibits a synergistic effect on the inhibition of growth of the pathogenic bacteria.

TABLE 1

*Escherichia coli* TK-3 strain

| Methicillin sodium (μg/ml) | 200 | 100 | 50 | 25 | 12.5 | 6.25 | 3.13 | 1.56 | 0.78 | 0 |
|---|---|---|---|---|---|---|---|---|---|---|
| 3200 | − | − | − | − | + | + | + | + | + | + |
| 1600 | − | − | − | − | + | + | + | + | + | + |
| 800 | − | − | − | − | + | + | + | + | + | + |
| 400 | − | − | − | − | + | + | + | + | + | + |
| 200 | − | − | − | − | + | + | + | + | + | + |
| 100 | − | − | − | + | + | + | + | + | + | + |
| 50 | − | − | − | + | + | + | + | + | + | + |
| 25 | − | + | + | + | + | + | + | + | + | + |
| 12.5 | − | + | + | + | + | + | + | + | + | + |
| 0 | + | + | + | + | + | + | + | + | + | + |

(μg/ml) T-1551 Na

TABLE 2

*Klebsiella pneumoniae* Y-4 strain

| Methicillin sodium (μg/ml) | 200 | 100 | 50 | 25 | 12.5 | 6.25 | 3.13 | 1.56 | 0.78 | 0 |
|---|---|---|---|---|---|---|---|---|---|---|
| 3200 | − | − | − | − | + | + | + | + | + | + |
| 1600 | − | − | − | − | + | + | + | + | + | + |
| 800 | − | − | − | − | + | + | + | + | + | + |
| 400 | − | − | − | + | + | + | + | + | + | + |
| 200 | − | − | + | + | + | + | + | + | + | + |
| 100 | − | − | + | + | + | + | + | + | + | + |
| 50 | − | − | + | + | + | + | + | + | + | + |
| 25 | − | − | + | + | + | + | + | + | + | + |
| 12.5 | − | − | + | + | + | + | + | + | + | + |
| 0 | + | + | + | + | + | + | + | + | + | + |

(μg/ml) T-1551 Na

TABLE 3

*Pseudomonas aeruginosa* S-111 strain

| Methicillin sodium (μg/ml) | | | | | | | | | | |
|---|---|---|---|---|---|---|---|---|---|---|
| 3200 | − | − | − | − | − | + | + | + | + | + |
| 1600 | − | − | − | − | − | + | + | + | + | + |
| 800 | − | − | − | − | + | + | + | + | + | + |
| 400 | − | − | − | + | + | + | + | + | + | + |
| 200 | − | − | − | + | + | + | + | + | + | + |
| 100 | − | − | − | + | + | + | + | + | + | + |
| 50 | − | − | − | + | + | + | + | + | + | + |
| 25 | − | + | + | + | + | + | + | + | + | + |
| 12.5 | + | + | + | + | + | + | + | + | + | + |

TABLE 3-continued

| Pseudomonas aeruginosa S-111 strain | | | | | | | | | | |
|---|---|---|---|---|---|---|---|---|---|---|
| 0 | + | + | + | + | + | + | + | + | + | + |
| | 200 | 100 | 50 | 25 | 12.5 | 6.25 | 3.13 | 1.56 | 0.78 | 0 |
| | | | | | (μg/ml) | | | | | |
| | | | | | T-1551 Na | | | | | |

Test Example 2

β-Lactamase specific activity

The β-lactamase activity was assayed by the iodometric assay method at 30° C., following the procedure of Perret [C. J. Perret, "Iodometric Assay of Penicillinase", Nature, 174, 1012 ∝ 1013 (1954)], except that a 0.1 molar phosphate buffer solution (pH 7.0) was used in place of the 0.2 molar phosphate buffer solution (pH 6.5). One unit of β-lactamase activity corresponds to the quantity of β-lactamase which decomposes 1 μmole/hour of T-1551 Na in a 0.1 molar phosphate buffer solution (pH 7.0) containing 8 mmoles of the substrate.

In Table 4, there are shown β-lactamase specific activities of *Escherichia coli* TK-3 strain, *Klebsiella pneumoniae* Y-4 strain and *Pseudomonas aeruginosa* S-111 strain.

TABLE 4

| Strain | β-Lactamase activity (unit/mg dry weight) |
|---|---|
| *Escherichia coli* TK-3 | 53 |
| *Klebsiella pneumoniae* Y-4 | 30 |
| *Pseudomonas aeruginosa* S-111 | 5.2 |

Test Example 3

ANTIBACTERIAL ACTIVITY AGAINST CLINICALLY ISOLATED STRAINS

The following test was performed to examine whether or not the synergistic effect of the present composition confirmed by the growth inhibition test in Test Example 1 is accompanied by an antibacterial effect.

A pathogenic bacterium was inoculated at a rate of about $10^8$ cells/ml into a Nutrient broth containing T-1551 Na (50 μg/ml) alone, T-1551 Na (25 μg/ml) plus Methicillin sodium (25 μg/ml) or Methicillin sodium (50 μg/ml) alone. The inoculated broth was incubated at 37° C. and the number of live cells in the culture broth was determined at predetermined time intervals.

Figure 1:
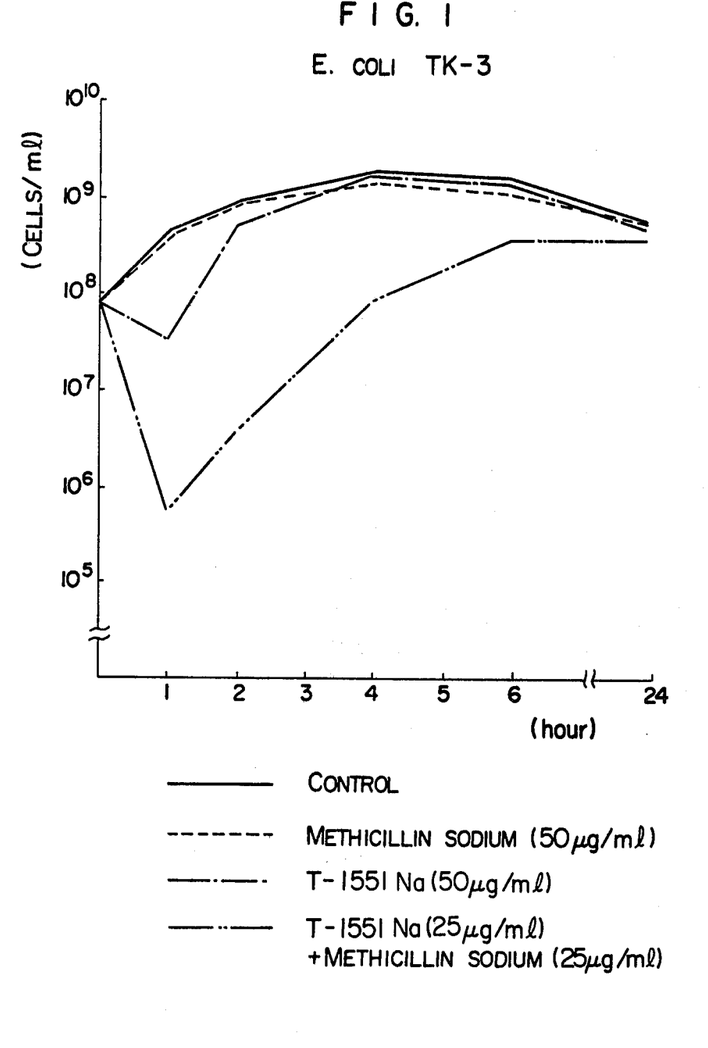
FIG. 1 shows antibacterial activities of sodium 7-[D(−)-α-(4-ethyl-2,3-dioxo-1-piperazinylcarbonylamino)-p-hydroxyphenylacetamide]-3-[5-(1-methyl-1,2,3,4-tetrazolyl)thiomethyl]-$\Delta^3$-cephem-4-carboxylate (referred to hereinafter as T-1551 Na) and Methicillin sodium against *Escherichia coli* TK-3, which is clinically isolated strain.
Figure 2:
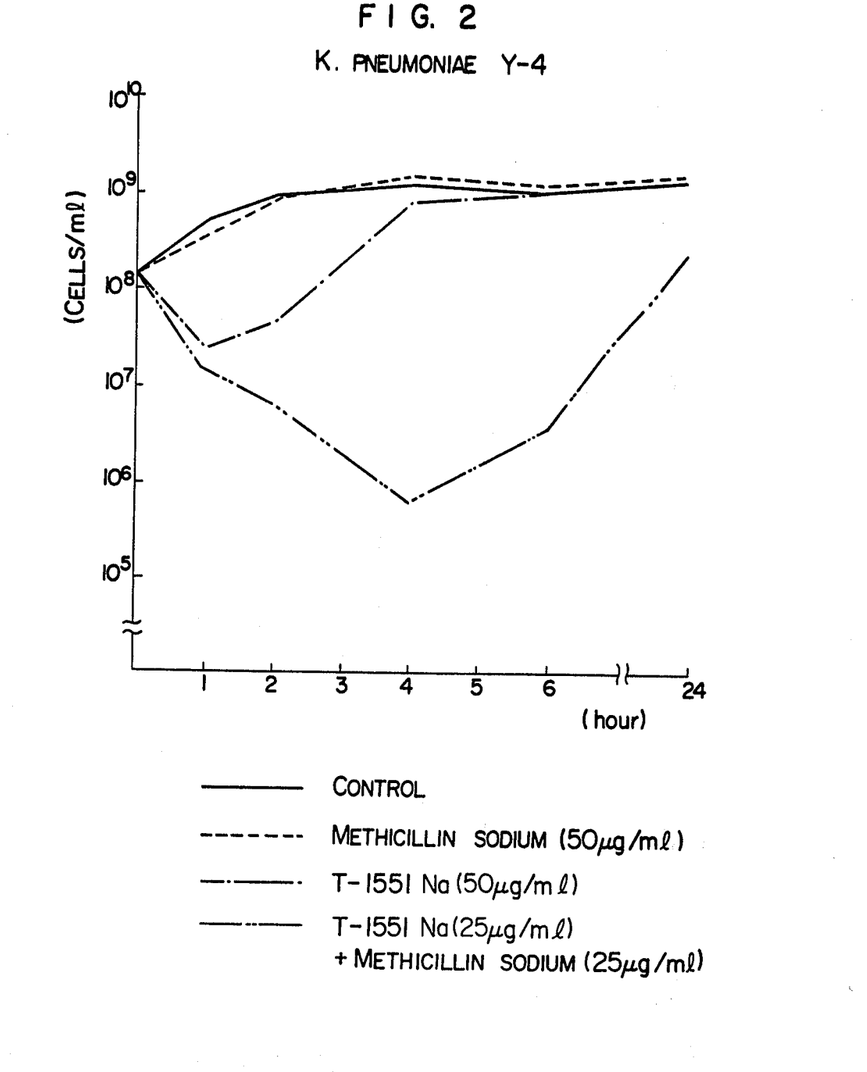
FIG. 2 shows those of T-1551 Na and Methicillin sodium against *Klebsiella pneumoniae* Y-4 which is clinically isolated strain.

The test results are as shown in FIGS. 1 and 2, and it was confirmed that the antibacterial activity had increased by the joint use of T-1551 Na and Methicillin sodium. The minimum inhibitory concentration of T-1551 Na or Methicillin sodium against *Escherichia coli* TK-3 strain or *Kleosiella pneumoniae* Y-4 strain was greater than 800 μg/ml in each case.

Test Example 4

EFFECT OF COMBINED USE ON EXPERIMENTAL INFECTION IN MICE

Male mice (5 mice per group) of the ICR strain, 4 weeks of age, were peritoneally inoculated with the prescribed number of pathogenic bacteria suspended in 5% mucin. After one hour and two hours following the inoculation, test preparations shown in Table 5 were subcuataneously administered to examine the protection effect. The results obtained were as shown in Table 5, wherein the protection effect was expressed in terms of $ED_{50}$.

TABLE 5

| Infectious bacterium | Challenge dose (cells/mouse) | $ED_{50}$, mg/mouse | | |
|---|---|---|---|---|
| | | T-1551 Na + Methicillin Na (2:1) | T-1551 Na | Methicillin Na |
| *K. pneumoniae* Y-4 | $5.7 \times 10^7$ | 4.8 | >26.8 | >50 |
| *K. pneumoniae* Y-53 | $1.0 \times 10^7$ | 1.66 | >10.0 | >46.6 |

As is apparent from Table 5, the synergistic effect of the combined use of T-1551 Na and Methicillin sodium on the inhibition of pathogenic bacteria growth, which had been found in vitro, was recognized also by the experiment of protection of animal from infection.

Text Example 5

The same operation as in Test Example 1 was repeated, except that the Methicillin sodium was replaced by potassium clavulanate and the test bacteria were replaced by those shown in Tables 6, 7 and 8, to obtain the results shown in Tables 6, 7 and 8.

TABLE 6

| | | *Escherichia coli* GN 6299 strain | | | | | | | | | | | |
|---|---|---|---|---|---|---|---|---|---|---|---|---|---|
| | (μg/ml) | | | | | | | | | | | | |
| Potassium clavulanate | 100 | − | − | − | − | − | − | − | − | − | − | − | − |
| | | − | − | − | − | − | − | − | − | − | − | − | + |
| | 25 | − | − | − | − | − | − | − | − | − | − | − | + |
| | | − | − | − | − | − | − | − | − | − | − | − | + |
| | 6.25 | − | − | − | − | − | − | − | − | − | − | − | + |
| | | − | − | − | − | − | − | − | − | − | − | − | + |
| | 1.6 | − | − | − | − | − | − | − | − | − | − | − | + |
| | | − | − | − | − | − | − | − | − | − | − | − | + |
| | 0.4 | − | − | − | − | − | − | − | − | − | − | + | + |
| | | − | − | − | − | − | − | − | − | − | + | + | + |
| | 0 | + | + | + | + | + | + | + | + | + | + | + | + |
| | | 800 | | 200 | | 50 | | 12.5 | 3.1 | | 0.8 | 0.2 | 0 |
| | | | | | | (μg/ml) | | | | | | | |
| | | | | | | T-1551 Na | | | | | | | |

TABLE 7

*Klebsiella pneumoniae* GN 69 strain

| Potassium clavulanate (μg/ml) | 800 | 200 | 50 | 12.5 | 3.1 | 0.8 | 0.2 | 0 |
|---|---|---|---|---|---|---|---|---|
| 100 | — | — | — | — | — | — | — | — |
|  | — | — | — | — | — | — | — | — |
| 25 | — | — | — | — | — | — | — | + |
|  | — | — | — | — | — | — | — | + |
| 6.25 | — | — | — | — | — | — | — | + |
|  | — | — | — | — | — | — | — | + |
| 1.6 | — | — | — | — | — | — | — | + |
|  | — | — | — | — | — | — | — | + |
| 0.4 | — | — | — | — | — | — | + | + |
|  | — | — | — | — | — | + | + | + |
| 0 | — | — | + | + | + | + | + | + |

(μg/ml) T-1551 Na

TABLE 8

*Pseudomonas aeruginosa* GN 3345 strain

| Potassium clavulanate (μg/ml) | 800 | 200 | 50 | 12.5 | 3.1 | 0 |
|---|---|---|---|---|---|---|
| 100 | — | — | — | — | — | — |
|  | — | — | — | — | — | — |
| 25 | — | — | — | — | — | — |
|  | — | — | — | — | — | — |
| 12.5 | — | — | — | — | + | + |
|  | — | — | — | — | + | + |
| 3.1 | — | — | — | — | + | + |
|  | — | — | — | — | + | + |
| 0.4 | — | — | — | — | + | + |
|  | — | — | — | + | + | + |
| 0 | — | — | + | + | + | + |

(μg/ml) T-1551 Na

Test Example 6

Figure 3:
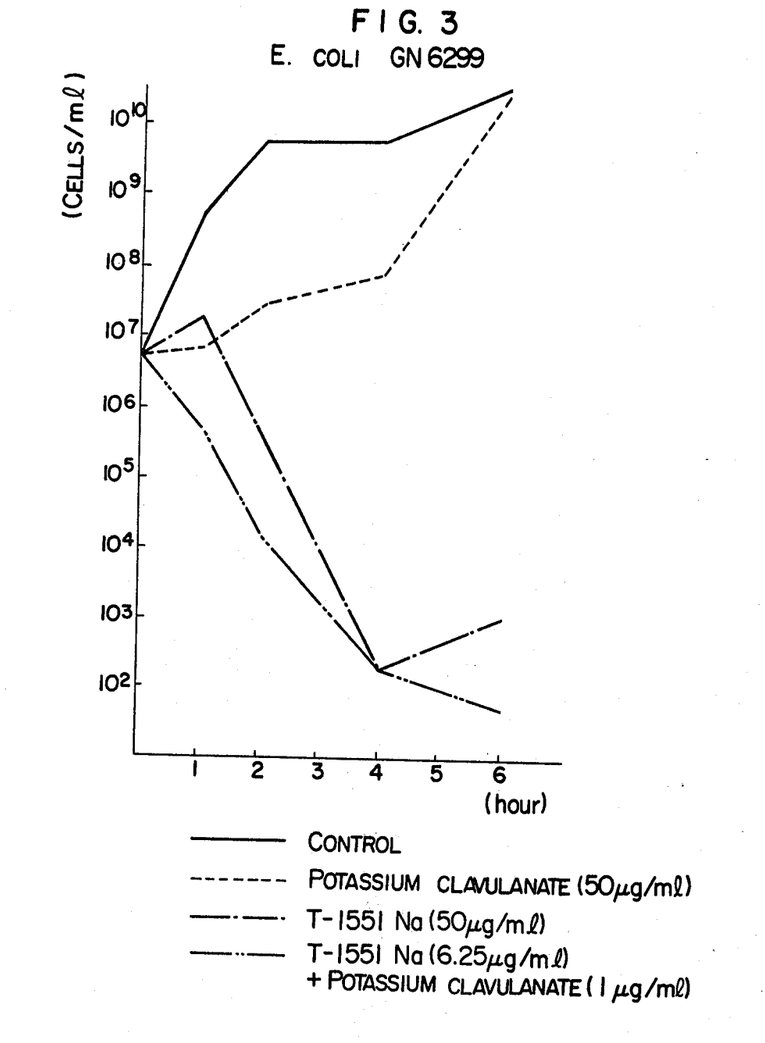
FIG. 3 shows those of T-1551 Na and potassium clavulanate against *Escherichia coli* GN 6299 which is clinically isolated strain.
Figure 4:
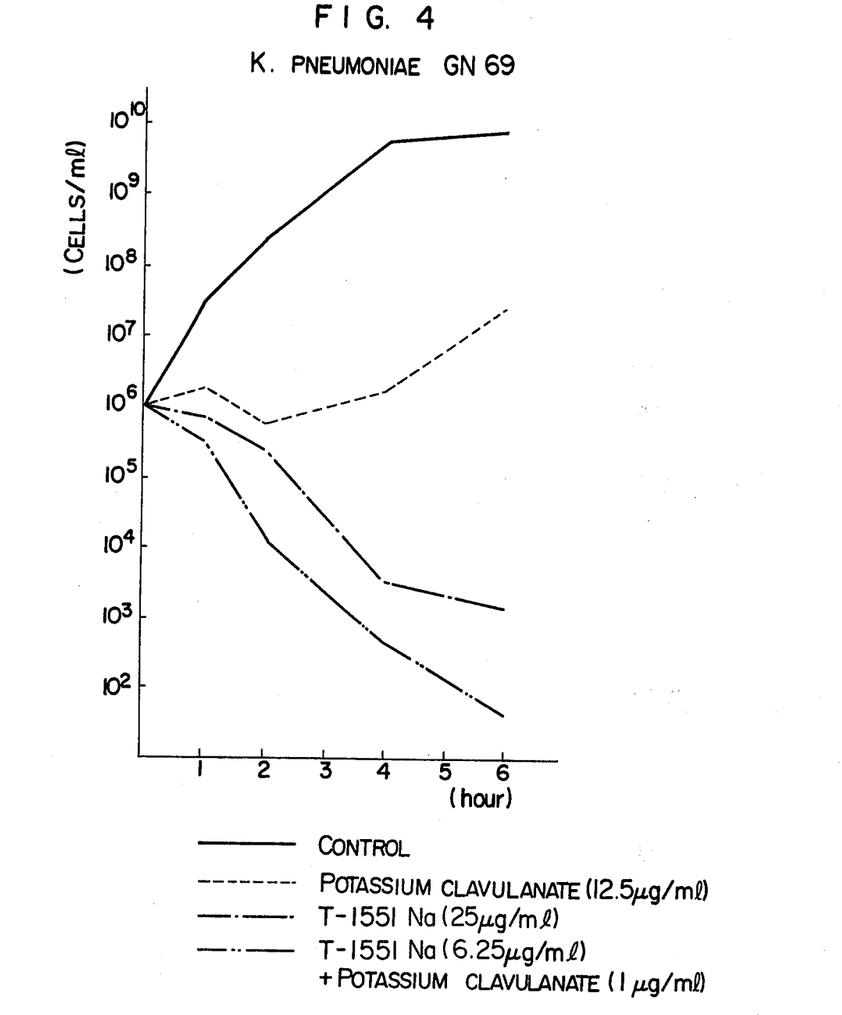
FIG. 4 shows those of T-1551 Na and potassium clavulanate against *Klebsiella pneumoniae* GN 69 which clinically isolated strain.
Figure 5:
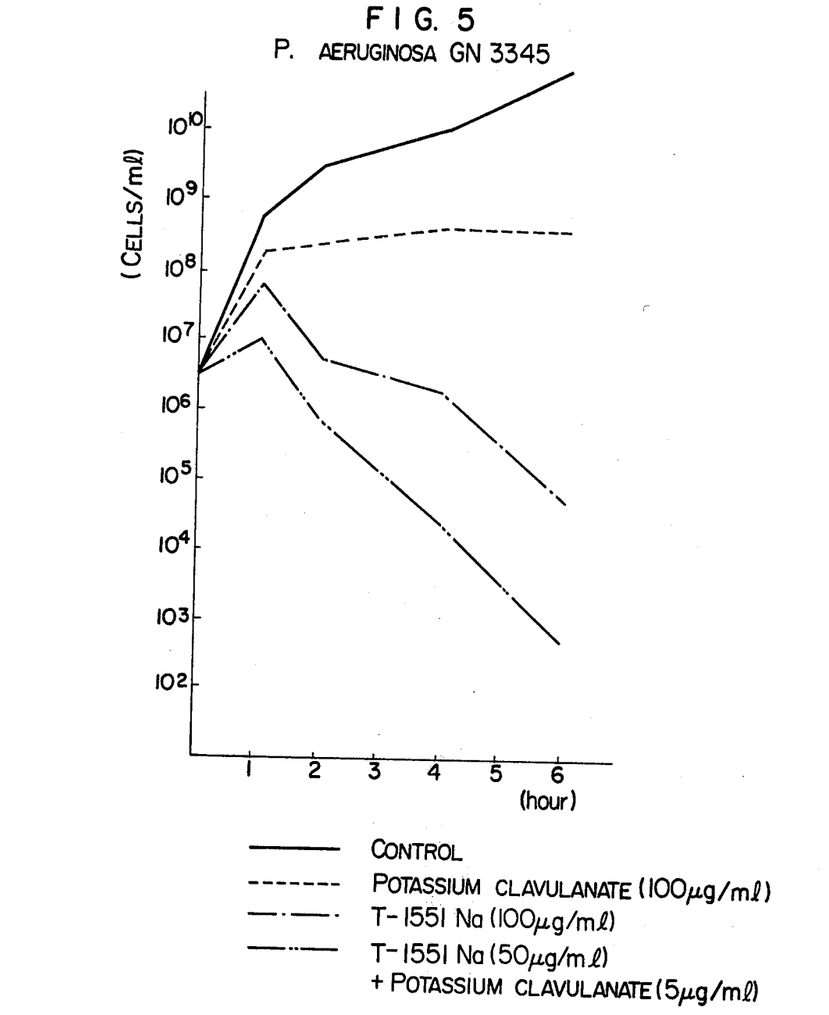
FIG. 5 shows those of T-1551 Na and potassium clavulanate against *Pseudomonas aeruginosa* GN 3345 which is clinically isolated strain.

The same operation as in Test Example 3 was repeated, except that the Methicillin sodium was replaced by potassium clavulanate, the pathogenic bacteria were replaced by those shown in FIGS. 3 to 5, and they were inoculated at a rate of $10^6$ cells/ml instead of $10^8$ cells/mol, to obtain the results shown in FIGS. 3, 4 and 5.

The test results described in the foregoing Test Examples 1 to 6 are typical of the pharmacological activity of the antibacterial composition of this invention. When other β-lactamase-inhibiting compounds having a β-lactam ring such as Oxacillin, Cloxacillin, Dicloxacillin, Flucloxacillin, Cefoxitin, and 7β-(D-α-cyanomethylthioacetamido)-7α-methoxy-3-[5-(1-methyl-1,2,3,4-tetrazolyl)thiomethyl]-Δ³-cephem-4-carboxylic acid, and sodium salts thereof, there were obtained results similar to those obtained with Methicillin sodium and potassium clavulanate.

And when other cephalosporins represented by the formula [I] than T-1551 Na were used, there were obtained effects similar to those obtained with T-1551 Na.

From the foregoing description, it is understandable that the antibacterial composition for medical use according to this invention is expected to be effective in the therapy of various diseases, the causative organisms of which are bacteria sensitive to the respective penicillins and cephalosporins. Especially, the composition of this invention will be highly useful in the therapy of various diseases including, for example, those in the medical department and urological department which are casued by the bacteria, sensitive to the cephalosporins represented by the formula [I] or pharmaceutically acceptable salts thereof, particularly belonging to Gram-negative bacteria, (*Escherichia coli, Pseudomonas aeruginosa, Klebsiella pneumoniae,* Proteus species, etc.).

The present invention is illustrated below with reference to Examples which are merely illustrative and not limitative.

EXAMPLE 1

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 500 mg potency |
| Sterilized Methicillin sodium | 500 mg potency |

The above ingredients were dissolved in 4 ml of a solution containing 0.5% (W/V) of lidocaine hydrochloride to obtain an injectable solution to be diluted when used.

EXAMPLE 2

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
| Sterilized Methicillin sodium | 500 mg potency |

The above ingredients were dissolved in 20 ml of physiological saline solution to obtain an injectable solution.

EXAMPLE 3

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
| Sterilized Methicillin sodium | 1 g potency |

The above ingredients were dissolved in 20 ml of a 5% glucose solution to obtain an injectable solution.

EXAMPLE 4

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 2 g potency |
| Sterilized Methicillin sodium | 1 g potency |

The above ingredients were dissolved in 250 ml of a transfusion to obtain a drip infusion.

EXAMPLE 5

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 250 mg potency |
| Sterilized Methicillin sodium | 250 mg potency |

The above ingredients were dissolved in 20 ml of a physiological saline solution to obtain an injectable solution.

EXAMPLE 6

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
| Methicillin sodium | 500 mg potency |

The above ingredients were dissolved in 20 ml of distilled water and freeze-dried in a usual manner to obtain a composition. This composition was dissolved in 20 ml of physiological saline solution to obtain an injectable solution.

EXAMPLE 7

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
| Sterilized Cloxacillin sodium | 500 mg potency |

The above ingredients were dissolved in 20 ml of physiological saline solution to obtain an injectable solution.

EXAMPLE 8

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
| Sterilized Dicloxacillin sodium | 500 mg potency |

The above ingredients were dissolved in 20 ml of physiological saline solution to obtain an injectable solution.

EXAMPLE 9

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
| Sterilized Oxacillin sodium | 500 mg potency |

The above ingredients were dissolved in 20 ml of physiological saline solution to obtain an injectable solution.

EXAMPLE 10

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
| Sterilized Cefoxitin sodium | 500 mg potency |

The above ingredients were dissolved in 20 ml of physiological saline solution to obtain an injectable solution.

EXAMPLE 11

| | |
|---|---|
| Sterilized sodium 7-[D(—)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
| Sterilized Flucloxacillin sodium | 500 mg potency |

The above ingredients were dissolved in 20 ml of physiological saline solution to obtain an injectable solution.

EXAMPLE 12

| | |
|---|---|
| Sterilized sodium 7-[D(—)-α-(4-ethyl-2,3-dioxo-1-piperazinylcarbonylamino)-p-hydroxyphenylacetamido]-3-acetoxymethyl-Δ3-cephem-4-carboxylate | 1 g potency |
| Sterilized Methicillin sodium | 500 mg potency |

The above ingredients were dissolved in 20 ml of physiological saline solution to obtain an injectable solution.

EXAMPLE 13

| Sterilized sodium 7-[D(−)-α-(4-ethyl-2,3-dioxo-1-piperazinylcarbonylamino)-p-hydroxyphenylacetamido]-3-[2-(5-methyl-1,3,4-thiadiazolyl)thiomethyl]-Δ3-cephem-4-carboxylate | 1 g potency |
|---|---|
| Sterilized Methicillin sodium | 500 mg potency |

The above ingredients were dissolved in 20 ml of physiological saline solution to obtain an injectable solution.

EXAMPLE 14

| Sterilized sodium 7-[D(−)-α-(4-ethyl-2,3-dioxo-1-piperazinylcarbonylamino)-p-hydroxyphenylacetamido]-3-[5-(1-methyl-1,2,3,4-tetrazolyl)thiomethyl]-Δ3-cephem-4-carboxylate | 1 g potency |
|---|---|
| Sterilized potassium clavulanate | 300 mg potency |

The above ingredients were dissolved in 20 ml of physiological saline solution to obtain an injectable solution

What is claimed is:

1. An antibacterial composition for medical use comprising as active ingredients (A) a cephalosporin represented by the formula:

wherein $R^1$ is 5-(1-methyl-1,2,3,4-tetrazolyl)thio and $R^2$ represents a hydrogen atom or a hydroxy group or a pharmaceutically acceptable salt thereof and (B) a β-lactamase-inhibiting compound having a β-lactam ring selected from the group consisting of Methicillin and pharmaceutically acceptable salts thereof, and the ratio of ingredient (B) to ingredient (A) is from 0.1:1 to 2.0:1.

* * * * *

UNITED STATES PATENT AND TRADEMARK OFFICE
CERTIFICATE OF CORRECTION

PATENT NO. : 4,428,936

DATED : January 31, 1984

INVENTOR(S) : Isamu Saikawa et al

It is certified that error appears in the above-identified patent and that said Letters Patent is hereby corrected as shown below:

On the title page Related U. S. Application Data should read

-- [63] Continuation of Ser. No. 22,102, Mar. 20, 1979, abandoned. --

Signed and Sealed this

Twenty-fourth Day of April 1984

[SEAL]

Attest:

GERALD J. MOSSINGHOFF

Attesting Officer  Commissioner of Patents and Trademarks